United States Patent [19]

Berg

[11] 3,968,367
[45] July 6, 1976

[54] FILTER SYSTEM FOR INFRARED ANALYSIS

[75] Inventor: Richard E. Berg, Chanhassen, Minn.

[73] Assignee: Honeywell Inc., Minneapolis, Minn.

[22] Filed: Oct. 14, 1975

[21] Appl. No.: 621,921

Related U.S. Application Data

[63] Continuation of Ser. No. 506,080, Sept. 16, 1974, abandoned, which is a continuation of Ser. No. 368,131, June 8, 1973, abandoned.

[52] U.S. Cl. .................................. 250/339; 250/343
[51] Int. Cl.² ........................................... G01J 1/00
[58] Field of Search ........... 250/337, 343, 345, 510, 250/339

[56] References Cited
UNITED STATES PATENTS

| | | | |
|---|---|---|---|
| 2,674,696 | 4/1954 | Smith et al. | 250/345 |
| 2,999,929 | 9/1961 | Martin et al. | 250/345 |
| 3,014,129 | 12/1961 | Martin | 250/345 |
| 3,435,209 | 3/1969 | Keahl | 250/339 |
| 3,488,491 | 1/1970 | Schuman | 250/345 |
| 3,539,804 | 11/1970 | Billetdeau | 250/339 |

Primary Examiner—Alfred E. Smith
Assistant Examiner—Bruce C. Anderson
Attorney, Agent, or Firm—Charles G. Mersereau; Henry L. Hanson

[57] ABSTRACT

An improved filtering technique in the detection by infrared absorption of a weak infrared absorbing gas in the presence of a strong infrared absorbing gas in a common sample involves providing a bandpass filter having a passband centered on a strong absorption line of the weak absorbing gas of interest to enhance the absorption due to the presence of that gas in the sample and providing a bandpass filter having a passband offset from any strong absorption line associated with the strong infrared radiation absorbing gas of interest to thereby decrease and linearize the amount of absorption caused by the presence of that gas of interest in the sample.

2 Claims, 5 Drawing Figures

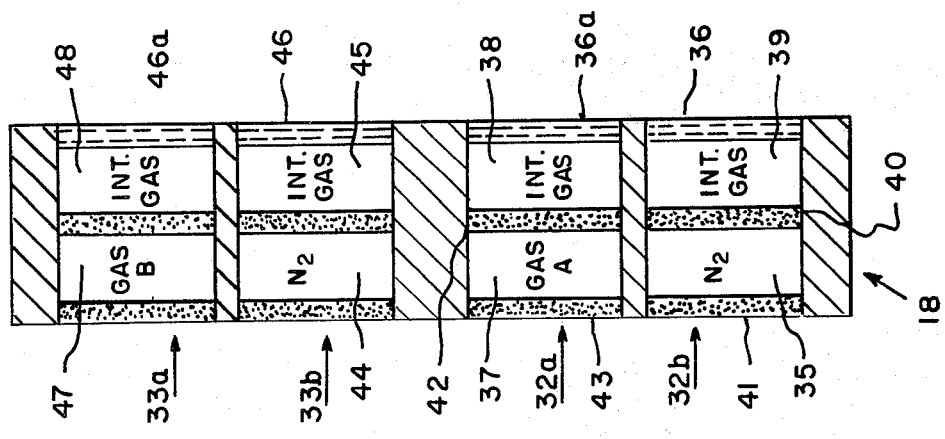
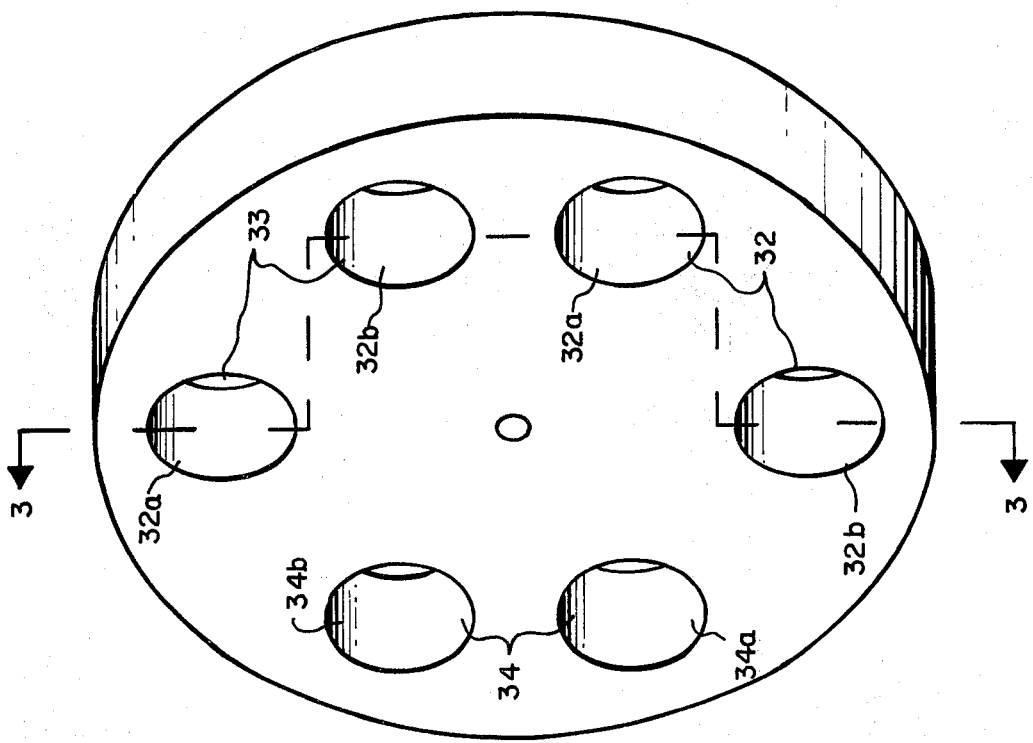

FILTER SYSTEM FOR INFRARED ANALYSIS

CROSS-REFERENCE TO RELATED APPLICATION

This is a continuation of application Ser. No. 506,080 filed Sept. 16, 1974 now abandoned which is a continuation of application Ser. No. 368,131 filed June 8, 1973 now abandoned.

Reference is made to the co-pending application by D. E. Benz, J. H. Garfunkel and A. D. Kompelien, Ser. No. 359,144, filed May 10, 1973, now U.S. Pat. No. 3,904,880, issued Sept. 9, 1975 and assigned to the same assignee, which is concerned with a multi-component non-dispersive infrared analyzer having a plurality of pairs of filters disposed in an infrared radiation path each pair providing a reference and an analysis filter for the analysis for a single designated gas of interest. Both the analysis and reference filters for the analysis for a given gas of interest contain bandpass filters having substantially the same passband, namely one containing at least in part a strong absorption line associated with the infrared absorption spectrum of the corresponding gas of interest. Thus, by that invention, bandpass filter elements having substantially identical passbands are provided in both the reference and analysis filters in the analysis for each gas of interest. To enhance specificity and sensitivity associated with the analysis of each of the gases of interest, the bandpass filters were selected to be centered on a strong absorption line in the particular infrared absorption spectrum associated with that gas of interest.

The present invention, on the other hand, is concerned with the solution of particular problems associated with the analysis for both weak infrared absorbing and strong infrared absorbing gases of interest within the same sample in a multicomponent infrared gas analysis apparatus.

BACKGROUND OF THE INVENTION

Field of the Invention

The present invention is related generally to the non-dispersive infrared analysis for a plurality of gases in a gaseous sample and, more particularly, to a filtering technique which may be utilized to improve the analysis for both strong and weak infrared absorbing gases in the presence of each other in a common sample.

Description of the Prior Art

It has long been known in the prior art that certain heteroatomic molecular species have individual characteristic infrared absorption spectra. It has also been known that such infrared absorbing species absorb infrared energy in an amount proportional to the number of molecules of that species present in a mixture of absorbing and non-absorbing constituents. In observing the characteristic infrared absorption spectra associated with various gases it has also been found that certain of these gases such as $CO_2$ are strong infrared absorbing gases while others such as CO are weak infrared absorbing gases. That is, a given percentage of $CO_2$ in a sample to be analyzed will inherently exhibit a much greater tendency to absorb infrared energy than the same percentage of CO from a band of infrared energy encompassing the absorption spectra of both gases.

A typical multi-component nondispersive infrared analyzer utilized to quantitatively determine a plurality of infrared absorbing species in a gaseous mixture typically derives such quantitative analysis from a comparison of intensity-related signals produced by the absorption of infrared radiation traversing reference and analysis filter systems. This is accomplished in a manner which renders the difference in intensity between the infrared energy traversing the reference filter system and analysis filter system dependent only upon the amount of the specific gas of interest in the sample. Thus, in the reference system, the infrared radiation normally traverses a cell containing a gas which does not absorb infrared radiation, for example, nitrogen followed by the sample cell containing a sample of the gas to be analyzed, and proceeds finally to a detector which is adapted to produce a signal in relation to the intensity of the infrared radiation impinging thereon. This signal is then compared with that produced by radiation traversing the analysis system including a sensitizing cell which contains the gas of interest, and the sample cell before impinging on the detector. This procedure may be repeated using numbers of pairs of filters corresponding to each gas of interest to be detected by the particular analytical instrument involved. Compensation may be made electronically or optically in the reference system for the amount of energy absorbed in the sensitizing cell of the analysis system.

A particular problem is encountered in adapting a device of the above or similar type to the quantitative determination of a rather high percentage of a strong infrared absorbing gas in the presence of a rather small percentage of a weak infrared absorbing gas present in a common sample. The infrared absorption from both gases is dependent upon both the inherent infrared absorption characteristics of the particular gas and the number of molecules of such gas present in the sample. A small percentage of a weak absorbing gas will produce far less of a reduction in the total infrared energy transmitted through the sample and a relatively high percentage of a strong absorbing gas. Thus, for example, in a mixture containing 25 per cent $CO_2$ and 1 per cent CO this discrepancy in signal reduction will reach several orders of magnitude. Accurate quantitative measure of both these species in a common sample by one analyzer would require a far greater range of linearity in both the detector and associated electronic signal processing components than is practical to achieve in such an instrument.

One technique that has been used in the prior art to overcome such a great discrepancy in infrared absorption by two gases of interest in a sample has been to actually subject the infrared radiation associated with the analysis for the weaker absorbing gas of interest to a greatly increased path length through the sample to increase the absorption therein as by using mirrors to pass that energy through the sample container several times. The resulting signal is then utilized to detect the weaker absorbing gas while the infrared radiation utilized to detect the stronger absorbing gas traverses the sample cell but once. Another such technique has been to utilize a plurality of sample cells. This technique involves providing an extremely long cell associated with the detection of a weak absorbing gas of interest and an extremely short cell associated with the detection of a strong absorbing gas of interest. This, of course, has the same effect inasmuch as it provides a difference in the path length through the sample traversed by the infrared radiation in the detection of a weak versus the detection of a strong infrared absorbing compound.

A further technique is illustrated and described in a patent to A. E. Martin No. 3,014,129 dated Dec. 19, 1961. That reference discloses a filtering technique which involves interposing a filter cell containing the gas of interest or a gas having a similar infrared absorption spectrum in the radiation path including the sample cell so that the amount of infrared radiation available for the strong absorbing gas to absorb in the sample is thereby reduced to a point where the signal produced by the strong absorbing gas is again lessened.

The last mentioned technique may be used with some success to linearize the portion of the absorbent curve corresponding to high percentages in the sample of strong absorbing gases such as $CO_2$, for example; however, that success is achieved at the expense of losing most if not all of the sensitivity in the instrument for low percentages of that gas of interest.

SUMMARY OF THE INVENTION

By means of the present invention problems associated with analysis for strong infrared absorbing components and weak infrared absorbing components in common gaseous sample are solved by the use of a special compensation filtering technique. Both the analysis and reference filter systems associated with the analysis of a weak infrared absorbing gas of interest are provided with a bandpass filter having a passband centered on a strong absorption line associated with the infrared absorption spectrum of that gas of interest. The reference and analysis paths associated with the analysis for a gas of interest having strong infrared absorption properties, on the other hand, are provided with a bandpass filter having a passband centered at an infrared wavelength offset from a strong infrared absorption line associated with that gas of interest. This technique enhances the relative amplitude of the output signal produced by the presence of a given percentage of the weakly absorbing gas of interest in the sample in relation to the signal produced in a like manner by the presence of a given percentage of the strongly absorbing gas of interest. By reducing the total operating signal range required for the strongly absorbing gas of interest, the required signal range over which the analytical instrument is required to operate is advantageously reduced and, at the same time, the relation between the output signal and the percentage of the strong absorbing gas in the sample is made more linear.

BRIEF DESCRIPTION OF THE DRAWINGS

FIG. 2 is a perspective view of the filter wheel of the invention;

FIG. 3 is a sectional view taken substantially along line 3—3 of FIG. 2;

DESCRIPTION OF THE PREFERRED EMBODIMENT

Figure 1:
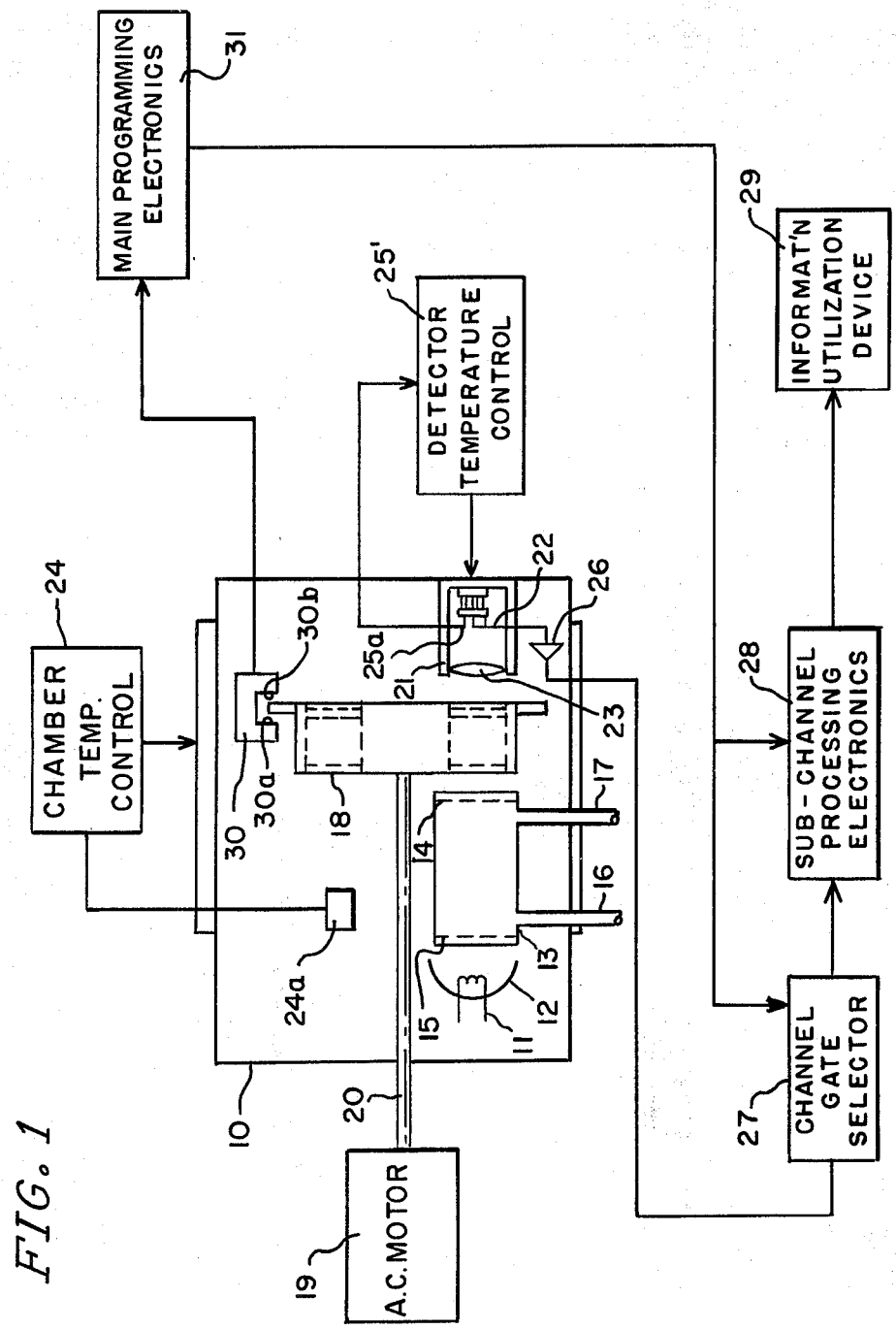
FIG. 1 is a schematic representation of the analyzing instrument of the present invention.

A system in which the filtering technique of the present invention may be used is described in conjunction with FIGS. 1–3.

FIG. 1 depicts an embodiment of an analyzer which can be used with the present invention in schematic form. In that figure, a housing 10 is provided which may contain the entire optical and all or part of the electronic system of the analyzer. The analyzer is provided with a source of infrared radiation 11 and, as discussed below, depending on the nature of that source, a reflector 12. A sample cell 13 having windows 14 and 15 which are transparent to the passage of infrared radiation and inlet and outlet accesses 16 and 17 is provided for containing the sample of the gas to be analyzed. A filter wheel 18, containing ordered pairs of filtering means as is required for the reference and analysis paths of each of the gases to be analyzed by the instrument is provided. The various components of the filter wheel are discussed below in greater detail. The filter wheel is driven in conjunction with the operation of the analyzer as by an AC motor 19 and drive shaft 20. A detector chamber 21 contains an infrared detector 22 for detecting the infrared radiation transmitted along the path from the source 11 to the detector 22. A lens 23 may be provided to focus the transmitted infrared radiation on the detector 22.

If desired, a chamber temperature control 24 operated in conjunction with a temperature sensor 24a may be used to control the temperature in the analyzer chamber. While temperature control is not strictly required for the operation of the analyzer of the invention, it is desirable to maintain a fairly constant temperature within the chamber as a constant temperature environment enhances the operation of the device. Such control also allows the instrument to be subjected to a wider range of external environmental temperatures.

Likewise, a temperature control 25 may be provided to control the temperature of the detector 22 through a temperature sensor 25a. The detector of the preferred embodiment is a solid state device and, as with most other solid state detectors, the detector produces signals in response to the detection of infrared energy which are somewhat temperature dependent. An increase occurs in the detector signal corresponding to a given intensity of infrared energy detected as the detector temperature is lowered. For example, a signal corresponding to a given percentage of a gas of interest may double in amplitude when the detector is cooled from 25°C to 0°C. The signal quantity and quality produced at 25°C in normal applications of the detector of the invention, however, is sufficient to produce good results although cooling may be desired.

In regard to the source of infrared energy 11, that source should be one capable of delivering approximately 1 milliwatt of energy to the detector after accounting for intermediate absorption along the optical path. Success has been obtained using several different kinds of sources which may be provided in combination with a reflector 12. Thus, a large, hot source such as SiC, for example, may be provided without the need for any reflector. A small hot source such as five turns of 0.25 mm diameter Kanthal wire, wound on a 1 mm mandrel, for example, has been used with a crude reflector. A rather large, relatively cool source may also be used, provided that an efficient reflector is provided. Thus, the only requirement of the source is that a sufficient amount of infrared energy be provided commensurate with the detector used and intermediate path losses encountered.

The general requirements for the sample cell are that it have a reasonably small volume, be leak proof, not contain any dead spaces which might lead to difficulties in purging or inaccurate readings, be easily cleaned, and, of course, be inert to the constituents found in the sample. Windows 14 and 15, of course, must pass the wavelengths of infrared radiation which the gases in the sample absorb. A material such as sapphire, for example, meets this transparency requirement quite well. It has been found that the efficiency of infrared transmissions due to the sample cell may be enhanced by coating the inside of the cell, except the windows, with a material with a high reflectivity for infrared radiation. A sample cell having a high reflectance, of course, will transmit a higher percentage of the infrared energy it perceives along the path. This is helpful in reducing the intensity of the source required to operate the instrument of the invention. Thus, metals such as gold, for example, which do have a high infrared reflectance have been used successfully in obtaining this increased transmission. Of course, gas sampling may be accomplished either in an on line continuous mode or in a batchwise fashion.

In certain applications of the analyzer it may be desired to monitor the environmental gaseous mixture in which the device is placed. Under such circumstances the sample cell will not be necessary and can be eliminated from the system allowing the environmental gas to be analyzed directly.

Detector 22 may be any one of a number of nonselective devices, i.e., devices which respond to a relatively broad band of the infrared spectrum not limited to the spectrum of a particular absorbing component, and which produce an electrical signal in response to the detection of infrared energy. The detector should have its peak sensitivity in the range of the infrared spectrum in which the gases of interest to be analyzed also have a high absorbance. The response of the detector must be relatively rapid and the output produced must have a high signal-to-noise ratio in order for the analyzing instrument to provide a fast and accurate gas analysis. One material meeting all the requirements of such a detector is the material mercury cadmium telluride (Hg,Cd)Te. One type of detector of this material has been found to have a peak response to infrared energy occurring at approximately 4.8 microns but has an excellent response over the entire range of from about 1.0 to above 5.4 microns. This range encompasses the infrared spectrum required to analyze samples for all of the common heteroatomic gases normally sought by such devices, for example, wavelengths include 3.3 microns for $CH_4$, 4.3 microns for $CO_2$ and 4.7 microns for $CO$. The response time i.e., the time it takes the detector output to build to about 63 percent of equilibrium value, of the (Hg,Cd)Te detector is relatively rapid (in the order of a few microseconds) and the detector exhibits an excellent signal-to-noise ratio. As discussed above, the detector may be cooled, if desired, to enhance the amplitude of a given response output.

Generally, the signal from the infrared detector 22 is conducted through a detector amplifier system 26 (discussed in greater detail below). Such amplified signals are then fed to a channel gate selection system 27 which sequentially selects a subchannel for the signal processing, one subchannel being provided for each gas to be analyzed. The signal is, in turn, fed to the proper subchannel electronic system for that particular gas as at 28 where the signal is further amplified and processed before being fed to an information utilization device 29 which may be a meter or other conventional output display. Synchronization between the channel gate selection system and the remaining channel processing electronics in relation to the position of the filter wheel 18 is also provided. The synchronization system includes a filter wheel position sensing device. The system 30 may include a light emitting diode 30a 30a and silicon detector optically actuated switch 30b. The system 30 feeds into the main programming electronics 31 which provide the required synchronization.

The filter wheel of the analyzer of the invention is illustrated in greater detail in FIGS. 2 and 3. FIG. 2 shows an enlarged perspective view of the filter wheel 18 of FIG. 1. The filter wheel is typically in the form of a machined circular disc-shaped member having a plurality of openings therethrough arranged in ordered pairs. Normally the openings are further arranged in a symmetrical radial pattern equi-distant from the center of the filter wheel 18 and from each other. Each pair of the ordered pairs of filters denoted as 32, 33 and 34 in the filter wheel 18 provides a filter system including a reference filter and an analysis filter for the analysis of a given gas of interest. Thus, the ordered pairs of openings and filters which are denoted by 32a and 32b, 33a and 33b, and 34a and 34b. For example, filter system 32 containing openings 32a and 32b may form such a pair designed to analyze the gaseous mixture for a given gas A, system 33, containing openings 33a and 33b for a given gas B, etc. It can be seen in the sectional view of FIG. 5 that each of the filters in the filter wheel 18 may contain a plurality of in-line filter elements.

As previously discussed, the analyzer of the invention is one which electronically compares electrical signals produced by the detection of infrared radiation traversing analysis and reference systems. Thus, as the filter wheel 18 rotates, the openings in the filter wheel are caused to pass sequentially into the path of infrared radiation between the source and the detector, aligned with the sample cell.

In general applications, if we designate opening 32b as one containing the reference filter for a given gas A, this reference filter normally includes several elements, namely a first cell 35 containing a gas transparent to infrared, for example, nitrogen and a narrow bandpass optical filter element 36 which filters out the entire infrared spectrum with exception of a narrow passband which contains at least one strong absorption line of the particular gas of interest A, to be detected. The analysis filter 32a in a like manner includes several elements, including a first or sensitizing cell 37 filled with the particular gas of interest, in this case, gas A. Filter 32a is also provided with a narrow bandpass optical filter element 36a which passes the same passband of infrared radiation as the narrow bandpass optical filter element 36.

If a further correlation filter is required because of the possible presence of another gas in the sample which has an infrared absorption spectrum overlapping that of the gas of interest in the narrow passband of the narrow bandpass filters, additional filter element chambers as 38 and 39 may be provided in both filters. These are filled with this interfering gas so that its presence in the sample will not affect the detector output signal in either path. Electronic compensation is made for the total energy difference between the reference and analysis systems caused by the absorption in cell 37.

Gastight windows 40 to 43 are provided to maintain the integrity of the gaseous species in the cells. The windows may be made of any gastight material which readily transmits infrared energy. Success has been achieved by utilizing sapphire windows secured in place as by a resin of epichlorohydrin in a well-known manner. A similar type resin, of course, can be used to fix the narrow bandpass optical filters 36 and 36a in place. Valves, not shown, may be machined in from the edge of the filter wheel 18 to provide access to and a seal for the plurality of chambers therein.

In similar fashion, the two filters 33a and 33b involved in the analysis of gas B provide an analysis filter and a reference filter respectively for that gas. The reference filter contains infrared-transparent gas cell 44, interfering gas cell 45, if required, and narrow bandpass optical filter 46. The analysis filter contains sensitizing gas cell 47, containing a pure specimen of the gas "B", interference gas cell 48, if required, and a narrow bandpass optical filter 46a. Of course, the narrow bandpass filters 46 and 46a should be adapted to pass the same narrow passband of the infrared spectrum, namely, one wherein gas B has at least one strong absorption line. This will generally be a different narrow passband from that passed by narrow bandpass filters 36 and 36a.

Again, using one gas A as an example, as the filter wheel 18 rotates assuming counterclockwise rotation, the detector will receive energy transmitted through filters 32a and 32b sequentially. Thus, a beam of infrared radiation passing through the sample chamber 13, sensitizing cell 37, gas filter cell 38 and narrow bandpass filter 36a will be detected by detector 22 during the time that sequence is established by the position of the filter wheel. Subsequently, when opening 32b is placed in the path, the detector will receive infrared energy passing through the sample cell 13, reference cell 35, gas filter cell 39 and narrow bandpass optical filter 36. This sequence, of course, repeats for the other optical filtering systems 33 and 34 in the analysis of the other gases of interest. Although the filter wheel pictured in FIGS. 2 and 3 represents one adapted for the analysis of three gases, having three ordered pairs of openings, it can readily be seen how any practical number of gases can be analyzed in a like manner by providing more or fewer numbers of ordered pairs of such openings in the filter wheel.

An important aspect of the present invention is directed to solving the problem of analyzing for both weak and strong infrared absorbing gases in a given single sample. As explained above, in a so-called dual-path nondispersive infrared analyzer utilizing a nonselective detector a quantitative measurement of each gas of interest by the analyzer is normally dependent upon a comparison of infrared-intensity related output signals produced through reference and analysis filtering systems associated with each gas of interest for which the sample is to be analyzed. Thus, associated with the analysis for each gas of interest, the intensity of infrared energy passed through a filter cell as at 37 and 47 (FIG. 3) containing a pure specimen of the gas of interest and the sample is compared to the intensity of like infrared energy traversing a reference filter cell as at 35 and 45 which may be evacuated or filled with an infrared transparent gas such as nitrogen. The removal of the great portion of the infrared spectrum associated with the particular gas of interest in the filter cell containing the pure specimen of the gas renders the difference in intensity in the infrared radiation striking a detector 22 having an infrared-intensity related output signal directly related to the absorption of infrared radiation in the sample cell by a particular gas of interest. Such a system is more fully illustrated and described in the above cross-referenced application.

In addition to the above, selected narrow bandpass optical filters as at 36, 36a and 46, 46a, respectively, which pass a narrow portion of the infrared spectrum to concentrate on a narrow band containing at least in part a strong absorption line of the particular gas of interest have been used to increase both the specificity and sensitivity of such an analytical instrument. By narrowing the band of infrared energy transmitted to the detector to one which is tailored to a strong absorption line of a gas of interest and doing so in both the reference and analysis filter systems, the total infrared energy traversing both systems is selectively reduced but the relative difference therebetween greatly enhanced when a quantity of the gas of interest is present in the sample. This, of course, increases the sensitivity of the device. By using a narrow infrared spectral band, specificity is also increased by decreasing the possibility of other gases which may be present in the sample, having infrared absorption spectra which overlap that of the gas of interest in the particular narrow band selected.

There is another advantage of using narrow bandpass optical filters in both the filtering systems which pass the energy to be compared ultimately by the detector. The advantage lies in the fact that errors resulting from spectral shifts caused by changes in the source output or detector response are practically eliminated because both systems are normally equally affected in such a narrow passband.

As mentioned above, however, a serious drawback to the use of such a system may occur when it is desired to analyze a given sample for both gases of interest which are strong absorbers of infrared energy such as $CO_2$ and ones which are relatively weak absorbers of infrared energy such as CO especially where the percentage of the strong absorbing gas likely to be present in the sample is greater than that of the weak absorbing gas such as might occur in the analysis of typical oxidation products of organic materials. In such cases, as stated, the ratio of the infrared energy reaching a given detector through reference and analysis filter systems utilized in the analysis on the strong infrared absorbing gas of interest may be several orders of magnitude greater than that achieved in the analysis of the relatively weak infrared absorbing gas of interest due to the inherent differences in absorption of the two gaseous species and relative quantities thereof present in the sample. The addition of the narrow bandpass filters in both the reference and analysis filter system which, as explained above, is otherwise advantageous further increases this ratio thereby adding to the problem. Thus, signal processing systems such as that described in the abovementioned cross-referenced application, it becomes quite difficult to tailor such an instrument both to the detection of a small amount or relatively weak absorbing gas in a large amount of a relatively strong absorbing gas in a common sample.

It is an important aspect of the present invention not only to solve the above problem but also to preserve all the advantages associated with the utilization of a narrow passband of the infrared spectrum in the analysis of each gas of interest in a multi-component gas analysis system. According to the present invention this is accomplished without drastic changes in the analysis apparatus such as shortening the path length of the infrared energy through the strong absorbing gas, using multiple sources, detectors or a signal processing system or the like all of which represent complex or radical methods of overcoming the problems associated with the need to cover larger infrared intensity ranges. The present invention accomplishes a dramatic result simply and without changing the source, the sampling technique or the detection and signal analysis systems.

By the present invention the narrow bandpass optical filters associated with the detection of a strong infrared absorbing gases of interest are employed which have passbands which are not centered on any strong absorption line of that gas of interest. Rather, it has been found that if the passbands used are spectrally offset from such strong absorption lines to reduce the corresponding ratio signals for strong infrared absorbing gases and centered on strong absorption lines in the analysis for relatively weak infrared absorbing gases, the problems associated with the analysis of a single sample for both may be greatly reduced.

Figure 4:
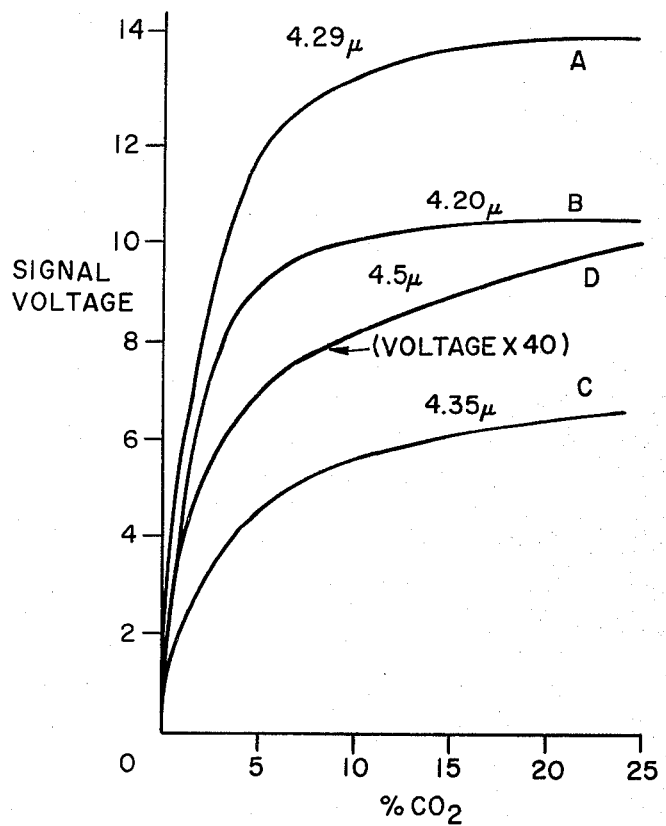
FIG. 4 depicts a series of curves of signal output voltage versus percentage of a strong absorbing gas showing the effect accomplished by changes in the passband of the bandpass filter.

Turning now to FIG. 4, we see a graphical representation of detector output voltage versus percentage composition of the strong absorbing gas $CO_2$ for several narrow passband optical filters. The voltage scale utilized on the graphical representation represents a ratio of the signal obtained without the presence of any of the gas of interest to one obtained from a sample containing a given percentage of the gas $CO_2$ in the sample. The closest strong absorption of $CO_2$ in relation to the narrow bandpass filters utilized in FIG. 1 occurs at approximately 4.3 $\mu$. Thus the bandpass filter of curve A having the passband centered on 4.29 $\mu$ is centered very close to the strongest part of this absorption line. It can readily be seen from the graph of FIG. 4 that as the passband of the narrow bandpass filter is shifted so as to be centered upon an infrared wavelength either shorter or longer and that associated with the strong absorption line for $CO_2$ a reduction in the signal occurs. Thus, by changing the center of the passband from 4.29 $\mu$ to 4.2 $\mu$ (curve B) the output voltage ratio for a sample containing 25 per cent $CO_2$ is reduced from approximately 13.8 volts to approximately 10.3, etc.

It should be noted that the most drastic reduction occurs in going to the 4.5 $\mu$ filter shown in curve D. The actual valve of which corresponds to 1/40 of that appearing on the graph as a different scale applies to that curve. Thus, with the narrow bandpass filter having a passband centered on 4.5 $\mu$ the ratio of the output voltage at 25 per cent $CO_2$ is reduced from 13.8 volts to approximately .245 volts, a value which is reduced from that of the 4.29 $\mu$ centered passband filter by a factor of approximately 56 to 1.

Thus, it can be seen from FIG. 4 that a significant reduction in such signal produced by a strong absorbing gas such as $CO_2$ can be accomplished by shifting the passband of the narrow passband filter used without having any effect on the analysis of any weak infrared absorbing gas which may also be present in the sample.

Of course, the particular bandpass filter selected for a given application will depend on several factors. This includes the relative percentages of a strong and weak infrared absorbing gases which a sample is anticipated to contain in the particular application of a multi-component gas analysis device. Also, a knowledge of the overall infrared spectrum of the strong absorbing gas must be known so that a correct bandpass filter may be selected in accordance with the locations of the various strong absorption lines of that gas. The locations of absorption lines in the spectra of possible interfering gases must also be considered although these may be eliminated by the use of other filtering techniques which are known in the art.

Figure 5:
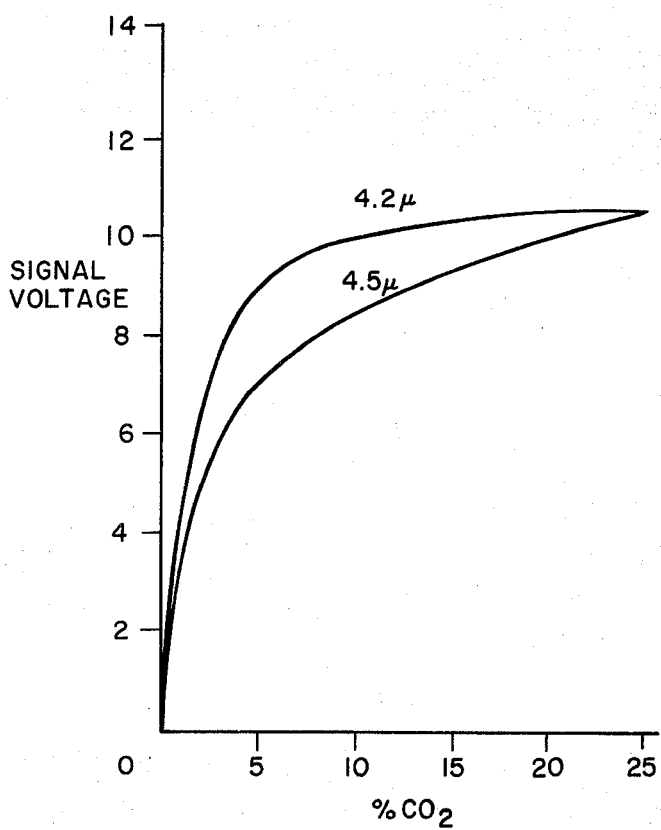
FIG. 5 is a normalized curve showing the linearizing effect of a change in the passband of the bandpass filter.

In FIG. 5 we see a "normalized" curve comparing the narrow bandpass filter centered on 4.5 $\mu$ with that centered on 4.2 $\mu$. To normalize the curve, the output voltage ratios obtained with the narrow passband filter centered on 4.5 $\mu$ have been multiplied by a common factor in order to achieve an identical reading with that of the 4.2 $\mu$ centered passband filter at the 25 per cent $CO_2$ point. From FIG. 5 it can be seen that in addition to greatly reducing the output ratio reading the 4.5 $\mu$ filter also accomplishes a linearizing effect in the curve which represents another advantage in utilizing an offset narrow bandpass filter in the situation.

The embodiments of the invention in which an exclusive property or right is claimed are defined as follows:

1. In a method of analyzing a gas sample for a plurality of gases of interest each of which has a characteristic infrared absorption spectrum associated therewith, wherein the analysis for each gas of interest is derived from a comparison of intensity-related signals produced by a detector means, wherein the difference in said signals is rendered dependent upon the absorption of infrared radiation from a source by that gas of interest; wherein at least one of said is a relatively strong absorbing gas and at least one of said gases of interest is relatively weak infrared absorbing gas and wherein the composition of said sample is such that a wide range exists in the relative values between intensity-related signals produced by said strong absorbing gas and said weak absorbing gas, the improvement comprising the step of:

reducing said wide range between said relative values between intensity-related signals produced by said strong absorbing gas and said weak absorbing gas by:

in the analysis for said strong infrared absorbing gas of interest, interposing bandpass optical filter means between said source and said detector means disposed such that radiation ultimately producing both of said intensity-related signals traverses said bandpass optical filter, said bandpass optical filter having a passband centered on an infrared wavelength which does not contain a strong absorption line of said strong infrared absorbing gas, and in the analysis for said weak infrared absorbing gas, interposing bandpass optical filter means between said source of infrared radiation and said detector means disposed such that said radiation ultimately producing each of said intensity-related signals traverses said bandpass optical filter, said bandpass filter having a passband centered on an infrared wavelength wherein said weak infrared absorbing gas strongly absorbs.

2. The method of claim 1 wherein the bandpass filter utilized in the analysis for a strong infrared absorbing gas is a passband offset from a strong absorption line of said strong infrared absorbing gas and wherein said bandpass optical filter utilized in the analysis of a weak infrared absorbing gas as a passband centered on a strong absorption line of said weak infrared absorbing gas.

* * * * *